United States Patent
Satoh (10) Patent No.: US 6,716,173 B2
(45) Date of Patent: Apr. 6, 2004

(54) ULTRASONIC IMAGING METHOD AND ULTRASONIC IMAGING APPARATUS

(75) Inventor: Tomoo Satoh, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/142,981

(22) Filed: May 13, 2002

(65) Prior Publication Data

US 2003/0004415 A1 Jan. 2, 2003

(30) Foreign Application Priority Data

May 14, 2001 (JP) ........................................ 2001-142705

(51) Int. Cl.[7] .............................................. A61B 8/02
(52) U.S. Cl. ........................ 600/447; 600/437; 600/443
(58) Field of Search ................... 600/437–472

(56) References Cited

U.S. PATENT DOCUMENTS

| | | | | |
|---|---|---|---|---|
| 4,456,982 A | * | 6/1984 | Tournois | 367/11 |
| 4,821,728 A | * | 4/1989 | Ledley | 600/447 |
| RE34,566 E | * | 3/1994 | Ledley | 600/443 |
| 5,379,642 A | * | 1/1995 | Reckwerdt et al. | 73/625 |
| 5,471,989 A | * | 12/1995 | Roundhill et al. | 600/440 |
| 5,967,985 A | * | 10/1999 | Hayakawa | 600/440 |
| 6,159,153 A | * | 12/2000 | Dubberstein et al. | 600/443 |
| 6,176,829 B1 | * | 1/2001 | Vilkomerson | 600/443 |
| 6,383,140 B1 | * | 5/2002 | Miwa et al. | 600/443 |

OTHER PUBLICATIONS

Hiroshi Kanda, et al. "Digital Ultrasonic Technology" the Japanese Journal of Clinical Radiology vol. 43, No. 11, 1998.

* cited by examiner

*Primary Examiner*—Dennis Ruhl
*Assistant Examiner*—William C Jung
(74) *Attorney, Agent, or Firm*—Sughrue Mion, PLLC (57) ABSTRACT

Ultrasonic imaging method and apparatus improved to provide image data at a high frame rate and achieve a better resolution. The ultrasonic imaging apparatus includes a transmission side signal processing unit for providing drive signals; an ultrasonic probe for transmitting ultrasonic beams and detecting echoes of the transmitted ultrasonic beams to obtain detection signals; a reception side signal processing unit for amplifying the detection signals and obtaining image data on the measurement target; and a control unit for controlling the transmission side signal processing unit to transmit ultrasonic beams simultaneously in a plurality of directions and controlling the reception side signal processing unit to process the detection signals and form a plurality of receiving focal points with respect to each of the transmitted ultrasonic beams.

14 Claims, 6 Drawing Sheets

ULTRASONIC IMAGING METHOD AND ULTRASONIC IMAGING APPARATUS

BACKGROUND OF THE INVENTION

1. Field of the Invention

The present invention relates to a method of ultrasonic imaging and an ultrasonic imaging apparatus for using ultrasonic waves in order to perform diagnosis of internal organs of living bodies or a non-destructive inspection.

2. Description of a Related Art

In general, an ultrasonic imaging apparatus including an ultrasonic diagnostic apparatus and industrial flaw detector uses an ultrasonic probe including a plurality of ultrasonic transducers with the functions of transmitting and receiving ultrasonic waves. The ultrasonic imaging apparatus with an ultrasonic probe uses a scanning line formed by combining ultrasonic waves to scan the objects in order to provide image data about an object to be inspected. In such an apparatus, two-dimensional or three-dimensional images of the object can be reproduced on the basis of the image data.

In such an ultrasonic imaging apparatus, as for the method of transmitting and receiving ultrasonic beams using an ultrasonic probe, the following two methods described in (1) and (2) have been known. In addition, the design of ultrasonic beam is described in "Digital Ultrasonic Technology" by H. Kanda et al., a special issue of the Japanese Journal of Clinical Radiology, Vol. 43, No. 11, pp. 1248–1252, published in 1998.

(1) Unidirectional ultrasonic beam transmission—Echo division receiving method

Figure 6A:
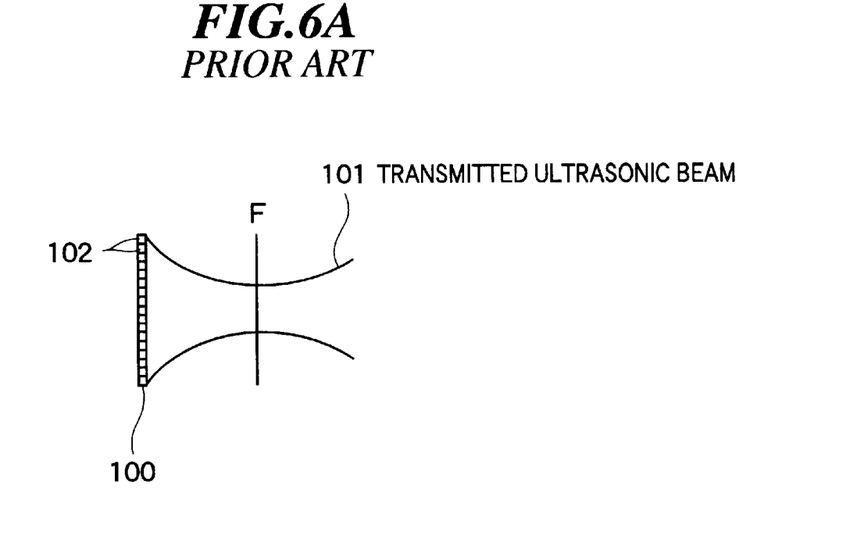
FIG. 6A is a schematic diagram illustrating an example of a transmitting state of an ultrasonic beam according to a conventional method.
Figure 6B:
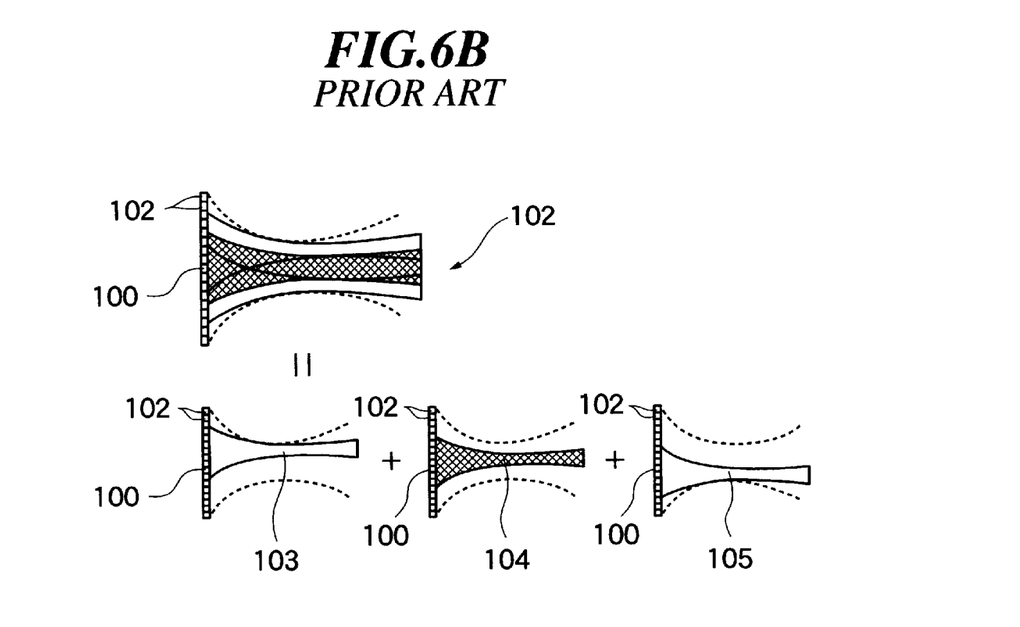
FIG. 6B is a schematic diagram illustrating an example of a receiving state of an ultrasonic beam according to a conventional method.

FIG. 6A is a schematic diagram illustrating an example of ultrasonic beam transmitting states according to a conventional method. Likewise, FIG. 6B is a schematic diagram illustrating an example of ultrasonic beam receiving states.

In this method, each of plural ultrasonic transducers 102 included in an ultrasonic probe 100 transmits ultrasonic pulses intermittently in accordance with drive signals supplied by a plurality of pulsers connected to a transmitting section. This ultrasonic pulse is transmitted from the ultrasonic probe 100 to the object to propagate through the object and form an ultrasonic beam 101, as shown in FIG. 6A. The ultrasonic beam 101 becomes narrower as it travels in the transmission source nearby area and narrowest at the focal point F, and thereafter diverges progressively. The ultrasonic beam is reflected by a reflector in the object to generate an echo. The ultrasonic probe 100, as shown in FIG. 6B, receives this echo. The detection signals output from the plural ultrasonic transducers 102 included in the ultrasonic probe 100 undergo a predetermined delay through a plurality of phase matching calculating units connected to a receiving section and they are added to each other to provide a detection signal for each received ultrasonic beam. In this example, three received ultrasonic beams 103, 104, and 105 are illustrated.

(2) Multi-directional ultrasonic beam transmission—Echo undivision receiving method.

Figure 7:
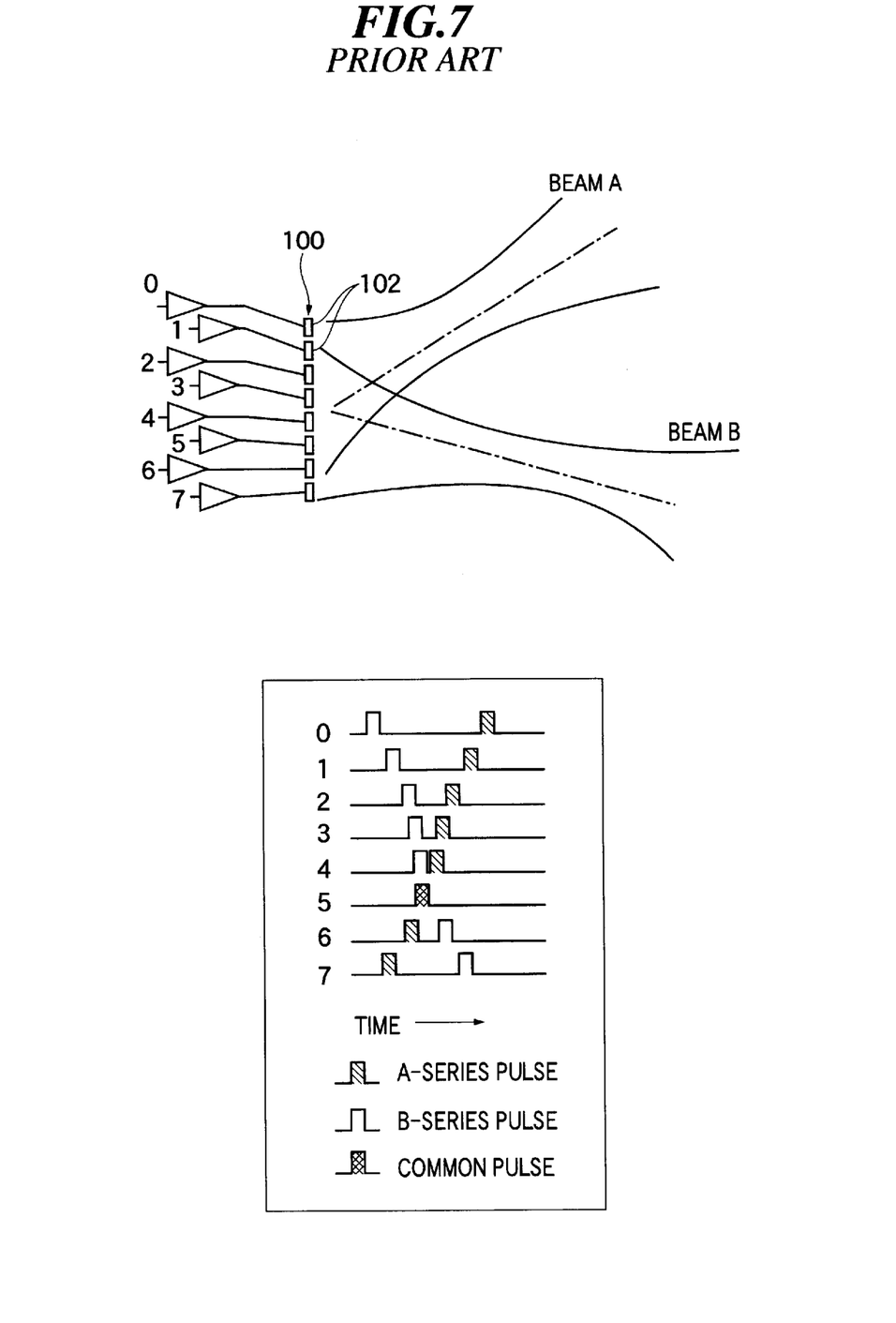
FIG. 7 is a schematic diagram illustrating another example of transmitting and receiving states of an ultrasonic beam according to a conventional method.

FIG. 7 is a schematic diagram illustrating another example of ultrasonic beam transmitting and receiving states according to a conventional method.

In this method, an ultrasonic probe 100 is supplied with two or more kinds of drive signals, whereby a plurality of ultrasonic transducers 102 included in the ultrasonic probe 100 are simultaneously supplied with more than one kind of drive signals by pulser sets. For example, as shown in FIG. 7, two sets of timing pulses composed of A-series pulses and B-series pulses are applied to one set of elements to generate both of an ultrasonic beam A and ultrasonic beam B. When the A-series pulses and the B-series pulses overlap one another, a common pulse is produced. These ultrasonic beams A and B are transmitted toward the object simultaneously in a plurality of directions, e.g. two directions.

For above-described ultrasonic diagnostic method and ultrasonic diagnostic apparatus, it has been required to improve a frame rate and resolution in recent years.

SUMMARY OF THE INVENTION

The invention was made in consideration of the foregoing. The first object of the invention is to provide an ultrasonic imaging method and an ultrasonic imaging apparatus which can obtain image data with a high frame rate. Further, the second object of the invention is to improve resolution in the ultrasonic imaging method and an ultrasonic imaging apparatus as mentioned above.

To solve the challenges above described, an ultrasonic imaging method according to the invention, of scanning a measurement target in an object to be inspected by using ultrasonic beams and receiving echoes of the ultrasonic beams reflected by the measurement target to obtain image data on the measurement target, comprises the steps of: (a) transmitting ultrasonic beams simultaneously in a plurality of directions toward the measurement target; and (b) processing detection signals obtained by detecting the echoes so as to form a plurality of receiving focal points with respect to each of the transmitted ultrasonic beams.

In addition, an ultrasonic imaging apparatus according to the invention, for scanning a measurement target in an object to be inspected by using ultrasonic beams and receiving echoes of the ultrasonic beams reflected by the measurement target to obtain image data on the measurement target, comprises: transmission side signal processing means for providing drive signals; an ultrasonic probe for transmitting ultrasonic beams by using a plurality of ultrasonic transducer elements in accordance with the drive signals provided by the transmission side signal processing means and detecting echoes of the transmitted ultrasonic beams to obtain detection signals; reception side signal processing means for amplifying the detection signals output from the ultrasonic probe and obtaining image data on the measurement target on the basis of the amplified detection signals; and control means for controlling the transmission side signal processing means to transmit ultrasonic beams simultaneously in a plurality of directions toward the measurement target from the plurality of ultrasonic transducer elements and controlling the reception side signal processing means to process the detection signals obtained by ultrasonic probe and form a plurality of receiving focal points with respect to each of the transmitted ultrasonic beams.

According to the invention, it is possible to increase the number of ultrasonic beam transmit/receive operations to be performed per unit time and to perform ultrasonic imaging at a high frame rate.

DESCRIPTION OF THE PREFERRED EMBODIMENTS

Referring now to the accompanying drawings, the embodiments of the invention will be described below in detail. In those drawings, the same components are identified by the same reference numeral with no description thereof.

Figure 1:
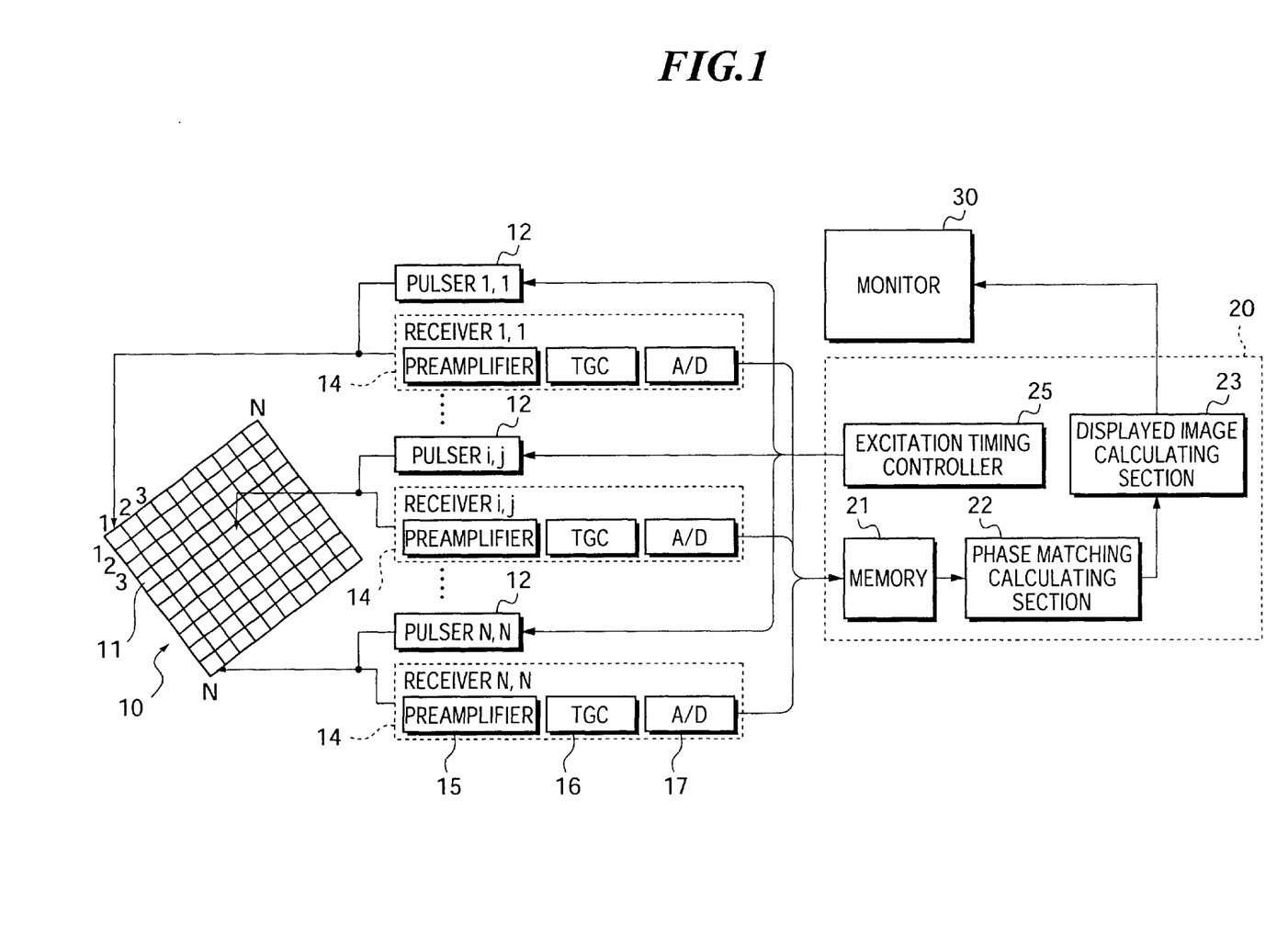
FIG. 1 is a block diagram illustrating the configuration of an ultrasonic imaging apparatus according to an embodiment of the invention.

FIG. 1 is a block diagram illustrating the configuration of an ultrasonic imaging apparatus according to an embodiment of the invention. This ultrasonic imaging apparatus is, for example, used as an ultrasonic diagnostic apparatus for the examination of human bodies or an industrial flaw detector.

As shown in FIG. 1, the ultrasonic imaging apparatus has an ultrasonic probe 10 that is used in contact with an object to be inspected. The ultrasonic probe 10 shown in FIG. 1 is a so-called two-dimensional array of transducers comprising a plurality, namely N×N=$N^2$, of ultrasonic transducers 11 having the functions of transmitting and receiving ultrasonic waves. In the ultrasonic probe 10, the ultrasonic transducers 11 may be arranged, for example, in the form of a two-dimensional matrix of N×N. The ultrasonic transducer 11 may include a piezoelectric device made out of the material such as PZT (lead zirconate titanate) or PVDF (polyvinyl difluoride). On applying a voltage, a piezoelectric device produces small mechanical vibrations to generate ultrasonic pulses. Contrarily, applying ultrasonic pulses across a piezoelectric device cause it to mechanically vibrate and generate an electrical signal (detection signal).

Alternatively, the ultrasonic probe 10 may be constituted by such piezoelectric devices used as ultrasonic transmitting devices and ultrasonic receiving devices such as Fabry-Perot resonators (hereinafter referred to as FPR) or fiber Bragg gratings, each formed at the tips of fine optical fibers. Although a two-dimensional array of transducers is used in this example, arrays other than such array, e.g. one-dimensional or one-and-a-half-dimensional array may be used.

N2 ultrasonic transducers 11 are connected with N2 pulsers 12 and N2 receivers 14 respectively.

Each of the pulsers 12 is excited according to an output signal of an excitation timing controller 25 incorporated in a system control section 20, which will be described below, and then outputs a drive signal to the corresponding ultrasonic transducer 11 of the ultrasonic probe 10. Each of the ultrasonic transducers 11 transmits an ultrasonic pulse to the object in accordance with a drive signal input from the corresponding pulser 12 and receives the ultrasonic pulse reflected by the object and outputs a detection signal. These pulsers are high-speed pulsers that can continuously output drive signals at a high repetition period (e.g. 3 MHz to 10 MHz).

Each of the receivers 14 comprises a preamplifier 15, TGC (time gain compensation) amplifier 16, and an analog-to-digital converter 17. The detection signals output from individual ultrasonic transducers 11 undergo analog processing in the preamplifiers 15 and the TGC amplifiers 16 included in the corresponding receivers 14. In this analog processing, levels of the detection signals are matched to the input signal levels of respective analog-to-digital converters 17. The analog signals output from the TGC amplifiers 16 are converted to digital signals (data) by the corresponding analog-to-digital converters 17 respectively.

The system control section 20 comprises a memory 21, a phase matching calculating section 22, a display image calculating section 23, and an excitation timing controller 25, and controls the entire system of the ultrasonic imaging apparatus.

The excitation timing controller 25 is connected to the individual pulsers 12 and the excitation timing controller outputs the signals for exciting the pulsers 12 individually. In this embodiment, the excitation timing controller 25 is constituted by an electronic circuit but may be constituted otherwise, for example, by a pattern generator. Controlling the excitation timing controller 25 enables excitation timing control for transmitting ultrasonic beams in a plurality of directions during the time interval between the emission of ultrasonic beams by the ultrasonic probe 10 and coming-back thereof as echoes from the maximum imaging depth.

The memory 21 is connected with the individual receivers 14 to store detection data output from the analog-to-digital converter 17 in each receiver 14 temporarily.

The phase matching calculating section 22 performs computations to match the phase of detection data stored in the memory 21. Although the phase matching calculating section 22 is shown in the form of one block in FIG. 1, a plurality of systems are provided corresponding to the number of receiving focal points. In addition, each of the plurality of systems in the phase matching calculating section 22 may be constituted by a shift resistor delay line, a digital micro-delay unit, a software, or the combination thereof.

Now, the phase matching calculating section 22 performs received beam forming as follows. Each of the systems in the phase matching calculating section 22 delays detection data produced in accordance with the detection signals output by the ultrasonic transducer 11 by a predetermined delay time. As a result, two or more pieces of detection data produced by a series of ultrasonic transducers 11 included in the ultrasonic probe 10 are matched in phase. In addition, the phase matching calculating section 22 adds these pieces of detection data to each other in digital form. Thus, the phase matching calculating section 22 having the plurality of systems enables simultaneous reception focusing in a plurality of directions within the object.

The display image calculating section 23 carries out demodulation of detection waveforms, conversion to image data, a predetermined image processing and conversion of scan formats with respect to the data output from the phase matching calculating section 22. This makes it possible to convert image data in scanning line data spaces into physical space image data. In addition, the display image calculating section 23 obtains voxel data, which is data for a certain volume, from more than one piece of tomographic data and performs the calculations to display a three-dimensional image.

The display image calculating section 23 is connected to a monitor 30. The monitor 30 receives image data which have undergone scan format conversion in the display image calculating section 23, converts it to the analog signals through digital-to-analog conversion, and displays an image according to the resultant signals.

Figure 2A:
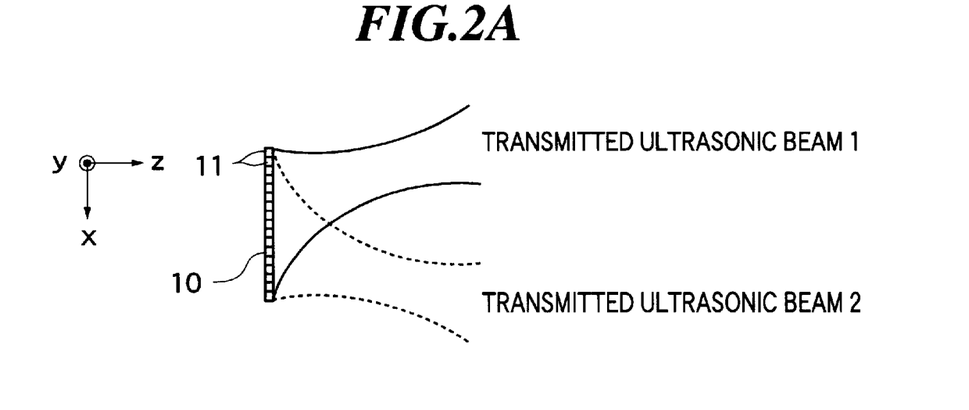
FIG. 2A is a schematic diagram illustrating a state in which ultrasonic beams are transmitted from the ultrasonic imaging apparatus shown in FIG. 1.
Figure 2B:
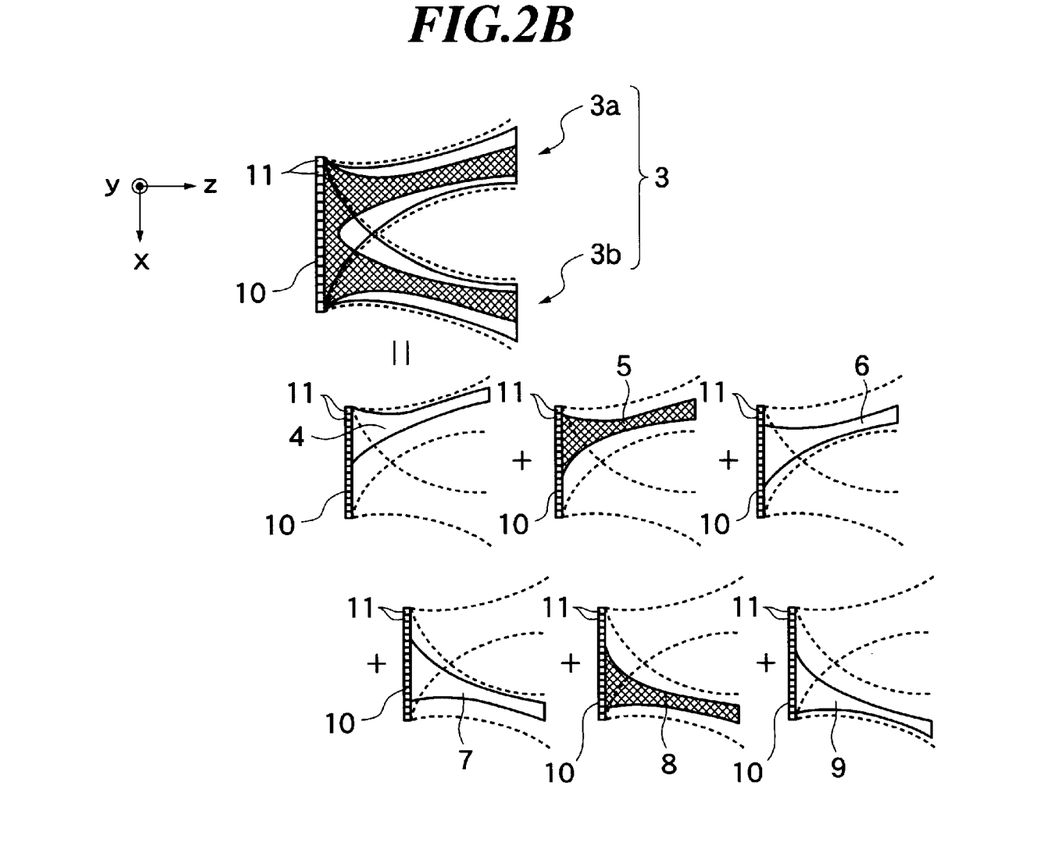
FIG. 2B is a schematic diagram illustrating a state in which ultrasonic beams are received by the ultrasonic imaging apparatus.

Now, the operation of the ultrasonic imaging apparatus according to the embodiment is described below. FIG. 2A illustrates a state in which two ultrasonic beams are transmitted from the ultrasonic imaging apparatus shown in FIG. 1. FIG. 2B illustrates a state in which the ultrasonic imaging apparatus receives echoes of ultrasonic beams.

First, ultrasonic beams are transmitted in different directions from the ultrasonic probe 10 shown in FIG. 1. In other words, a plurality of pursers 12 output continuous drive signals at a high repetition period, e.g. 3 MHz to 10 MHz, to the ultrasonic transducers 11 included in the ultrasonic probe 10 under control of the excitation timing controller 25 in the system control section 20 shown in FIG. 1. At that time, ultrasonic pulses may be transmitted from all of N2 ultrasonic transducers 11 or some of those transducers. In this embodiment, predetermined two sets of ultrasonic transducers belonging to the N2 ultrasonic transducers transmit ultrasonic pulses toward a measurement target within the object with their phases shifted each other.

Figure 3:
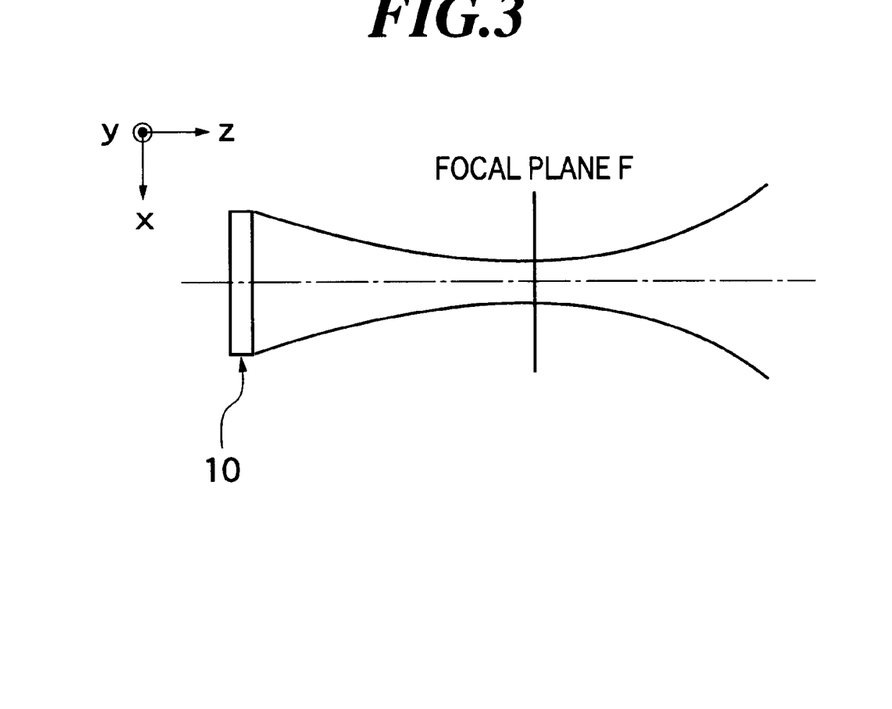
FIG. 3 is a schematic diagram for explanation of a form of a transmitted ultrasonic beam.

The ultrasonic pulses thus transmitted by two sets of the ultrasonic transducers form two transmitted ultrasonic beams 1 and 2 as shown in FIG. 2A. Referring now to FIG. 3, an ultrasonic beam becomes narrower as it travels in the transmission source nearby area and narrowest at the focal point F, and thereafter diverges progressively. Therefore, it is desired that an operator appropriately operates the ultrasonic probe 10 such that the focal point F of an ultrasonic beam is located on the measurement target within the object.

The ultrasonic beams 1 and 2 simultaneously transmitted in two directions from the ultrasonic probe 10 are reflected by the measurement target within the object, so that the ultrasonic probe 10 receives the echoes 3 as illustrated in FIG. 2B. The echoes 3 overlap one another when they are received by the ultrasonic probe 10, as shown in the upper portion of FIG. 2B. A plurality of ultrasonic transducers 11 output detection signals in accordance with the echoes 3 that the ultrasonic probe 10 has received.

Thereafter, the echoes 3 received by the ultrasonic probe 10 undergo the reception focusing. In other words, the detection signals of echoes 3 output by the ultrasonic transducers 11 are entered into their corresponding receivers 14 respectively. In those receivers 14, the respective detection signals are subjected to the analog processing in the preamplifier 15 and the TGC amplifier 16 thereof and matched to the input signal levels of the corresponding analog-to-digital converters 17. The output analog signals from the TGC amplifiers 16 are converted into their digital equivalents in the corresponding analog-to-digital converters 17, stored in the memory 21 temporarily, and then entered into the phase matching calculating section 22 in parallel.

Subsequently, the phase matching calculating section 22 performs the received beam forming based on a series of detection data produced on the basis of the echoes 3. That is to say, the phase matching calculating section 22 imparts a plurality sets of delays corresponding to the number of receiving focal points to a series of detection data stored in the memory 21 so that the received echo 3a corresponding to a transmitted ultrasonic beam 1 can form a plurality of receiving focal points by using the series of detection data stored in the memory 21. In addition, the phase matching calculating section 22 adds each set of delayed data up in digital form. As a result, three echoes 4–6 may be obtained from the echo 3a corresponding to a transmitted ultrasonic beam 1, as shown in FIG. 2B. The phase matching calculating section 22 also performs the received beam forming so that the received echo 3b corresponding to a transmitted ultrasonic beam 2 can form a plurality of receiving focal points. Thus, three echoes 7–9 may be obtained form the echo 3b.

Therefore, the number of image data obtained in one transmit/receive operation of ultrasonic beams is determined as follows. First, two types of detection signals are obtained by receiving the echoes 3a and 3b that correspond to ultrasonic beams 1 and 2 transmitted in two directions. Then, each type of signals is subjected to three different phase matching processes and divided into three varieties of data. Then, the number of image data is represented by the following expression:

(the number of directions of transmitted ultrasonic waves)×(the number into which an echo is divided)=2×3=6

As described above, it is possible to produce six types of image data in one transmit/receive operation of ultrasonic beams, which enables the improvement of frame rates by six times.

Figure 4:
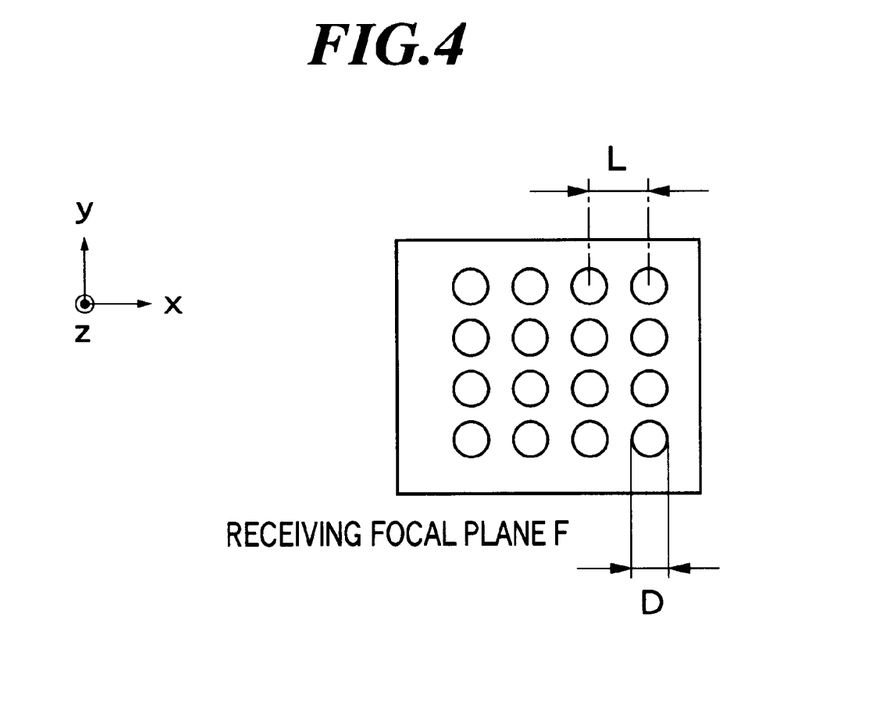
FIG. 4 is a view schematically illustrating a focal point cross section (receiving focal plane) of the received ultrasonic beams.

FIG. 4 schematically illustrates a focal point cross section (receiving focal plane) of the received ultrasonic beams which has been subjected to the received beams forming as described above. As shown in FIG. 4, a plurality of focal points formed by the received beam forming are placed in the focal plane. Now a beam diameter on an ultrasonic beam receiving focal plane F after the receiving beam forming is indicated with D, and a distance between receiving focal point centers of ultrasonic beams is represented with L. To separate focal points in the receiving focal plane F, it is necessary to control the excitation timing controller 25 in the system control section 20 so as to satisfy the requirement that L is greater than or equal to D.

Figure 5A:
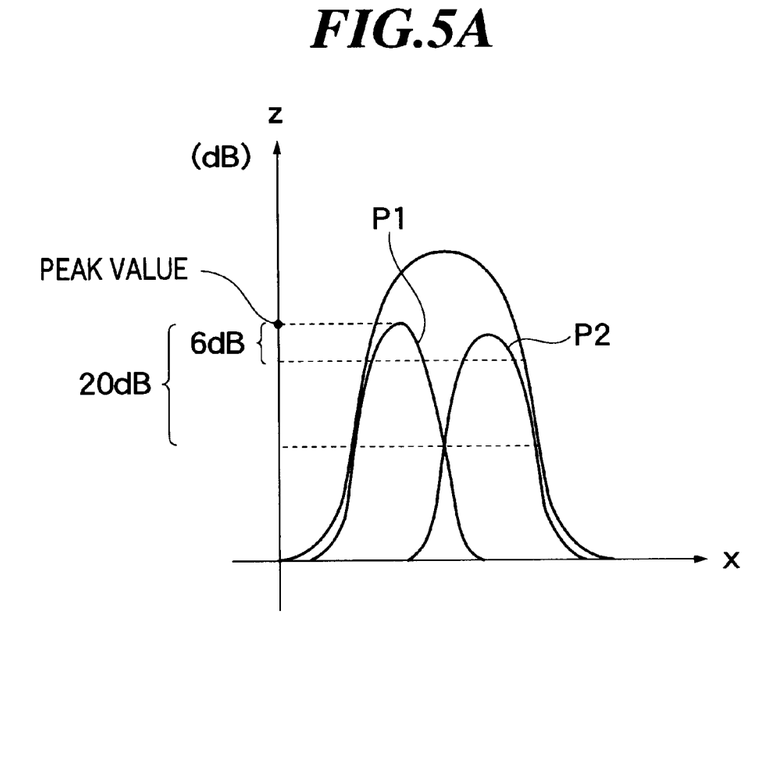
FIG. 5A shows an example of sound pressure distribution of ultrasonic beams received in an ultrasonic imaging method according to an embodiment of the invention.
Figure 5B:
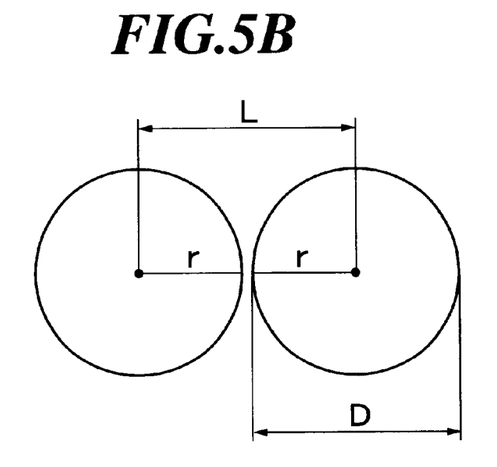
FIG. 5B shows a relation between the ultrasonic beams.

More specifically, the excitation timing of excitation timing controller 25 is controlled such that the distributions of two received ultrasonic beams P1 and P2 overlap one another in area where their sound pressures are at least 6 dB less than the sound pressure peak values of the received ultrasonic beams P1 and P2, preferably 20 dB or more less than the peak values, as shown in FIG. 5A. When the diameter of an ultrasonic beam is defined by a diameter at both ends of which an ultrasonic wave sound pressure become 6 dB or 20 dB less than the peak value thereof, a distance L between receiving focal point centers becomes larger than or equal to the sum of cross sectional diameters r of two ultrasonic beams P1 and P2 as shown in FIG. 5B. As a result, the ultrasonic beam P1 and P2 are separated. Therefore, the cross talk is reduced when separating the echoes reflected back from two directions by reception focusing.

The detection data, which have undergone the received beam forming in the phase matching calculating section 22 as described above, are subjected to detection of the detection waveform, conversion into the image data, predetermined image processing, and conversion of image data scan formats in the display image calculating section 23 which converts image data in scanning line data spaces into physical space image data. In addition, the display image calculating section 23 produces voxel data, which is data for a certain volume, from a plurality pieces of tomographic data and also calculates to display a three-dimensional image. Results of the calculations in display image calculating section 23 are converted into corresponding analog signals in the monitor 30 before displayed as images.

Although it has been described that, in a preferred embodiment of the invention, ultrasonic beams are simultaneously transmitted in two directions, it is also naturally possible to transmit ultrasonic beams in more directions at a time.

According to the invention, simultaneously transmitting a plurality of ultrasonic beams in various directions increases the number of ultrasonic beam transmit/receive operations to be performed per unit time, which enables high frame rate imaging. In addition, the excitation timing is controlled such that the ultrasonic beam distributions concerning a plurality of receiving focal points at the time of beam reception overlap one another in an area where their sound pressures are at least 6 dB less than the sound pressure peak values of the received ultrasonic beams, preferably 20 dB or more less than the peak values, therefore, it is possible to reduce cross talk between a plurality of received ultrasonic beams and to provide image data with a high resolution.

As described above, according to the invention it is possible to provide image data with a high frame rate or to improve resolution.

While the preferred embodiment of the invention has been described, it is to be understood that modification and variation thereof may be made without departing from the spirit and scope of the following claims.

What is claimed is:

1. An ultrasonic imaging method of scanning a measurement target in an object to be inspected by using ultrasonic beams and receiving echoes of the ultrasonic beams reflected by the measurement target to obtain image data on the measurement target, said method comprising the steps of:
   (a) transmitting a plurality of ultrasonic beams simultaneously in a plurality of respective directions toward the measurement target by using an ultrasonic probe having a plurality of ultrasonic transducer elements, each of said ultrasonic beams being formed of ultrasonic signals having their phases shifted from those in other of said ultrasonic beams at said plurality of ultrasonic transducer elements; and
   (b) processing detection signals obtained by detecting the echoes to generate signal data and subjecting each of the signal data to a plurality of phase matching processes so as to form a plurality of receiving focal points with respect to the transmitted ultrasonic beams.

2. An ultrasonic imaging method according to claim 1 wherein step (b) includes storing the signal data and subjecting each of the stored signal data to a plurality of delays, whereby a plurality of delayed signals are produced.

3. An ultrasonic imaging method according to claim 2 wherein step (b) further includes calculating said plurality of receiving focal points on the basis of said stored signal data and delayed data produced from said delayed signals.

4. An ultrasonic imaging method according to claim 1, wherein step (a) includes:
   transmitting the ultrasonic beams by using an ultrasonic probe having a plurality of ultrasonic transducer elements; and
   controlling transmission timing of said plurality of ultrasonic transducer elements such that cross talk between the detection signals obtained for the plurality of receiving focal points becomes not larger than a predetermined value.

5. An ultrasonic imaging method according to claim 4, wherein step (a) includes:
   controlling transmission timing of said plurality of ultrasonic transducer elements such that a distance between adjacent two ultrasonic beam centers in a receiving focal plane of the ultrasonic beams becomes not less than a beam diameter of each of the ultrasomc beams in the receiving focal plane after received beam forming.

6. An ultrasonic imaging method according to claim 5, wherein said beam diameter is defined by a diameter at both ends of which ultrasonic wave sound pressure after the received beam forming becomes 6 dB less than a peak thereof.

7. An ultrasonic imaging method according to claim 5, wherein said beam diameter is defined by a diameter at both ends of which ultrasonic wave sound pressure after the received beam forming becomes 20 dB less than a peak thereof.

8. An ultrasonic imaging apparatus for scanning a measurement target in an object to be inspected by using ultrasonic beams and receiving echoes of the ultrasonic beams reflected by the measurement target to obtain image data on the measurement target, said apparatus comprising:
   transmission side signal processing means for providing drive signals;
   an ultrasonic probe for transmitting a plurality of ultrasonic beams by using a plurality of ultrasonic transducer elements in accordance with the drive signals provided by said transmission side signal processing means and detecting echoes of the transmitted ultrasonic beams to obtain detection signals;
   reception side signal processing means for processing the detection signals output from said ultrasonic probe to generate signal data; and
   control means for controlling said transmission side signal processing means to transmit said plurality of ultrasonic beams simultaneously in a plurality of respective directions toward the measurement target from said plurality of ultrasonic transducer elements, each of said ultrasonic beams being formed of ultrasonic signals having their phases shifted from those in other of said ultrasonic beams at said plurality of ultrasonic transducer elements, and subjecting each of the signal data generated by said reception side signal processing means to a plurality of phase matching processes so as to form a plurality of receiving focal points with respect to the transmitted ultrasonic beams.

9. An ultrasonic imaging apparatus according to claim 8 wherein said control means includes:
   memory means for storing the signal data generated by said reception side signal processing means; and
   a phase matching calculating section for subjecting each of the stored signal data to a plurality of delays, whereby a plurality of delayed signals are produced.

10. An ultrasonic imaging apparatus according to claim 9 wherein said control means calculates said receiving focal points on the basis of said stored signal data and delayed data produced from said delayed signals.

11. An ultrasonic imaging apparatus according to claim 8, wherein said control means controls said transmission side signal processing means such that cross talk between the detection signals obtained for the plurality of receiving focal points becomes not larger than a predetermined value.

12. An ultrasonic imaging apparatus according to claim 11, wherein said control means controls said transmission side signal processing means such that a distance between centers of ultrasonic beams which are adjacent to each other in a receiving focal plane of the ultrasonic beams becomes, after received beam forming, not less than a beam diameter of each of the ultrasonic beams in the receiving focal plane.

13. An ultrasonic imaging apparatus according to claim 12, wherein said beam diameter is defined by a diameter at both ends of which ultrasonic wave sound pressure after the received beam forming becomes 6 dB less than a peak thereof.

14. An ultrasonic imaging apparatus according to claim 12, wherein said beam diameter is defined by a diameter at both ends of which ultrasonic wave sound pressure after the received beam forming becomes 20 dB less than a peak thereof.

* * * * *